United States Patent [19]

Bryant

[11] Patent Number: 4,769,608
[45] Date of Patent: Sep. 6, 1988

[54] SELF-CLEANING STREAMING CURRENT MONITOR

[76] Inventor: Robert L. Bryant, 5166 Meadowcreek Dr., Dunnwoody, Ga. 30338

[21] Appl. No.: 17,131
[22] Filed: Feb. 20, 1987
[51] Int. Cl.⁴ .......................... G01N 27/60; G01N 1/12
[52] U.S. Cl. ................................ 324/453; 73/863.82; 73/863.83
[58] Field of Search .......... 73/863.41, 863.42, 863.44, 73/863.82, 863.83, 864.34, 864.35, 864.81; 324/453, 464, 439, 447, 450

[56] References Cited

U.S. PATENT DOCUMENTS

| | | | |
|---|---|---|---|
| 3,184,973 | 5/1965 | Bradley | 73/863.83 |
| 3,812,722 | 5/1974 | Soudelier | 73/863.82 |
| 3,943,771 | 3/1976 | Handa | 73/863.41 |
| 4,269,064 | 5/1981 | Johnson | 73/862.82 |
| 4,446,435 | 5/1984 | Canzonieri | 324/453 |
| 4,449,101 | 5/1984 | Canzonieri | 324/453 |
| 4,631,967 | 12/1986 | Welker | 73/863.83 |

FOREIGN PATENT DOCUMENTS 0905697  2/1982  U.S.S.R. .......................... 73/863.41

Primary Examiner—Reinhard J. Eisenzopf
Assistant Examiner—Jose M. Solis
Attorney, Agent, or Firm—Harry I. Leon

[57] ABSTRACT

A streaming current detector which utilizes the test flow stream to keep the electrodes of the detector probe washed and its dielectric surfaces from becoming fouled. The test stream first enters a housing surrounding the probe at a position proximate the inlet to a transverse passageway within the probe. Most of the flow moves directly through the probe along the transverse passageway, but a small portion of this flow is sucked into capillary-sized channels within the probe by the action of a piston during its upstroke and then expelled from them back into the transverse passageway during the downstroke. The flow leaving the transverse passage plummets downwardly where it joins a smaller fraction of the test stream that did not enter the transverse passageway and together they are discharged out the bottom of the housing. There are no low velocity or stagnate areas where solids can accumulate either in the housing surrounding the probe or within the probe itself. The flow velocity is kept high everywhere so that floc which does come in contact with the probe is constantly washed off from the flow stream. In this manner, the inlet to the probe, its through passageway and its capillary-sized channels as well as the housing surrounding the probe are kept free from contamination allowing both a continuous operation and a higher electrical output. The higher electrical output makes possible a signal with remote sensing capabilities. This design answers the long standing problem of keeping a streaming current detector clean during operation.

7 Claims, 4 Drawing Sheets

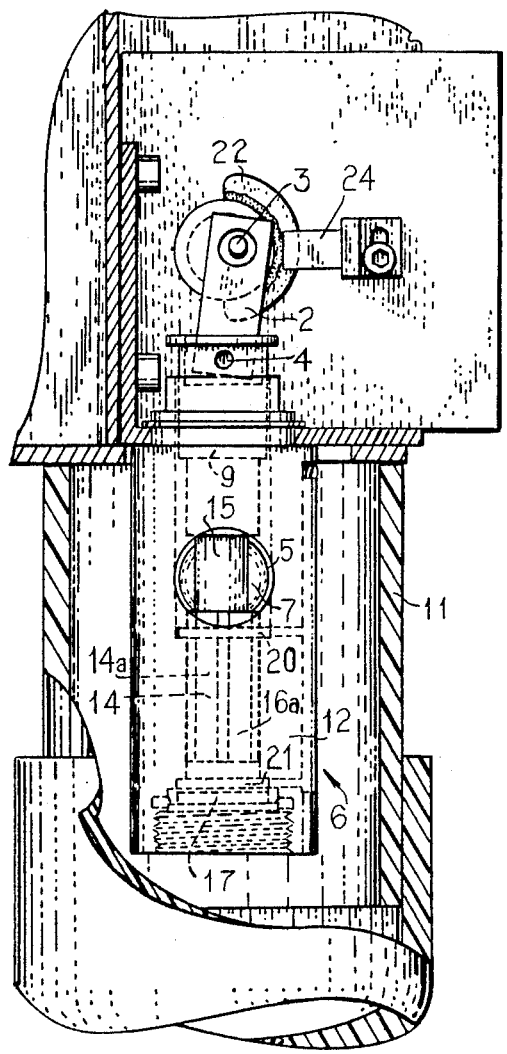
Fig. 3.
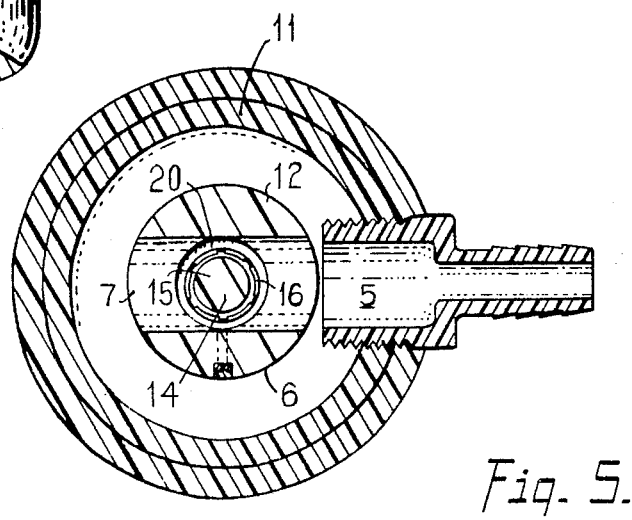
Fig. 4.
Fig. 5.

SELF-CLEANING STREAMING CURRENT MONITOR

BACKGROUND OF THE INVENTION

The present invention relates to an improved streaming current detector.

It is well known that most waters contain ions and other charged species such as colloids that give rise to a zeta potential on the surfac eof objects that form flow channels for these waters. When such a surface, in the presence of charged species in water, is moved past a pair of electrodes, a current is generated which is called the streaming current. This current is proportional to the net charge density of the water flow.

The measurement of the streaming current has long been recognized as useful in controlling the amount of chemicals needed to treat water for consumption or disposal. In order to make water clean enough for use, treatment chemicals are employed to change the charge density of the water so that contaminates in the water will form aggregates and settle out of the water as a floc. A variety of chemicals are used to clean water which may have a wide range of contaminates. In particular, raw water that is usually negatively charged is processed with coagulant chemicals such as alum to reduce the negative charge. In all cases, it is economically desirable to minimize the use of the chemicals for floc formation.

Once water has been chemically treated, any floc which forms has a tendency to stick to every surface with which it comes into contact, especially to horizontal surfaces. Unfortunately, if any floc is allowed to build up on a surface disposed proximate a probe in which the streaming current is being measured to evaluate the charge density of a flow stream, the sample will give an unreliable reading of the streaming current.

Many attempts have been made at keeping the probe and its electrodes clean during operation. One of the lastest is that of Canzoneri et. al., U.S. Pat. No. 4,446,435. Canzoneri uses an ultrasonic cleaner attached to a probe to clean the area around it during operation. The use of ultrasonic cleaning has been a partial success since it does tend to remove colloidal particles from the surfaces of the piston-electrode chamber where measurements upon a sample are made. However, Canzoneri failed to realize that his method of introducing the sample flow into the bottom of the housing of the probe and discharging this flow from the housing near the top of the probe was working against the natural flow of the floc with the result that the sample tended to be self-contaminating. Canzoneri, aware that his ultrasonic cleaner did not completely solve the electrode contamination problem, introduced a second invention in U.S. Pat. No. 4,449,101. In the latter device, he included a periodic wash in which a cleaning fluid was backflowed into the piston-electrode chamber. Although this backflow also helped to alleviate the contamination problem, its inclusion made the indicator system considerably more complicated.

A device in which the sample stream is introduced at the top of the probe and discharged downwardly from its side was disclosed by one of the earlier pioneers, Gerdes in U.S. Pat. No. 3,368,145. However, Gerdes allowed the sample stream to enter a reservoir about the pistonelectrode chamber within the probe so that some settling tended to occur before the sample flowed into the chamber.

Moore, U.S. Pat. No. 4,297,640, realized that noise is generated in the signal due to a buildup of floc near the top of the upper electrode as occurred in Gerdes' device. In order to minimize these effects, Moore placed a grounding electrode above the two sensing electrodes and between them and the point of floc buildup. This approach, while offering a remedy to a poorly designed sample flow inlet, greatly reduced the current that could have been produced in the absence of a grounding electrode resulting in a weaker signal.

SUMMARY OF THE INVENTION

An object of the present invention is to provide a streaming current detector having a probe with a well designed entrance that does not need to have a grounding electrode.

A further object of the present invention is to provide a streaming current detector which has a probe flow pattern that keeps the electrodes and the surrounding dielectric clean and free from contaminates that would otherwise reduce the signal strength, thereby allowing a readout and control device to be remotely situated from the sensing probe of the detector.

In accordance with the present invention, there is provided a very stable and reliable detector for measuring the streaming current of water or of wastewater that can operate over long periods of time without having to be shut down for cleaning. In this device, a portion of the test flow stream is directed so that it constantly washes a transverse passageway within a probe from which each sample is taken by its being sucked into capillary-sized channels within a piston-electrode chamber directly beneath the passageway. Moreover, in the present invention, the portion of the stream flowing in the transverse passageway moves over the entrances to these channels with sufficient velocity to wash away any floc that might form on the top of these entrances. Further, to maintain this flow velocity as high as possible, a segment of the piston above the electrodes has a waist.

The high flow velocity in the transverse passageway at the channel entrances also gives rise to a positive pressure in the flow crossing the top of these capillary-sized channels when the piston is in its up position and to a negative or suction pressure at the top of the capillary-sized channels when the piston is in the down position. This effect adds to the forces acting on the sample flow due to the piston reciprocating in the piston-electrode chamber and facilitates the ingress and egress of sample to and from the capillary-sized channels.

In addition, the test flow stream after leaving the transverse passageway at the top of the piston-electrode chamber drops into a housing surrounding the probe and is immediately discharged from the bottom of the housing before any floc or grit can build up. Thus not only is the flow of this stream at the inlet to the probe and throughout the transverse passageway above the piston-electrode chamber at a high velocity but also the flow exiting the probe is directed downward through a drain channel that provides for a discharge which is both rapid and in the direction toward which heavier particles tend naturally to settle, so that any floc or grit present remains suspended in the test flow stream or is immediately washed away. In this way, the measuring electrodes and the surfaces of the probe around them are kept free from contaminate buildup.

By keeping the test flow stream in rapid motion as it approaches the inlet to the probe and is subsequently discharged from it, not only is reduced downtime for cleaning realized with this improved detector but also the reliability of measurements made with it is increased over that of earlier detectors. Due to the large reduction in the contamination of the electrodes, a stronger signal can be generated. This increase in the signal strength allows the tranducer to be installed at large distances from the readout device; this combination has not been possible previously.

The stronger signal also provides for the inclusion of complex filtering circuits that greatly facilitate signal noise reduction thereby giving rise to a more reliable indication.

BRIEF DESCRIPTION OF THE DRAWINGS

Further details are explained below with the help of the examples illustrated in the attached drawings in which:

FIG. 3 is a cross-section III—III from FIG. 1;

FIG. 4 is a cross-section IV—IV through the probe in FIG. 2 on an enlarged scale;

FIG. 5 is a cross-section V—V from FIG. 2; and

DETAILED DESCRIPTION OF THE PREFERRED EMBODIMENT

Referring to the figures, there is shown an apparatus in accordance with the present invention for measuring the average net ionic and colloidal surface charge on the surface of an annulus formed of a dielectric material, the charge being a function of the charge influencing species, such as ions, charged molecules or colloidal particles, which are present in a liquid stream in flowing contact with said dielectric surface.

Figure 1:
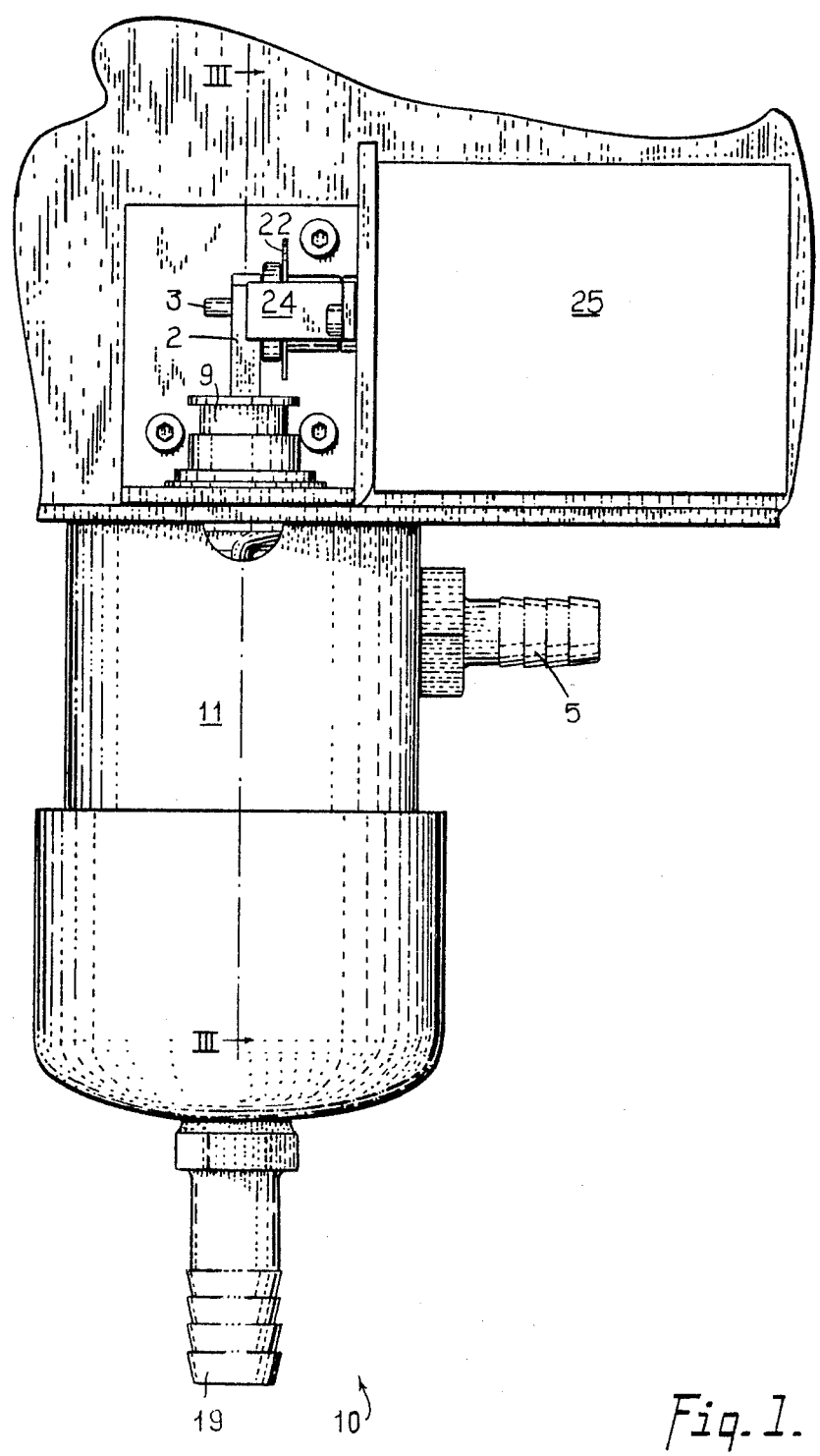
FIG. 1 is a frontal elevation view of the streaming current detector according to the present invention.
Figure 2:
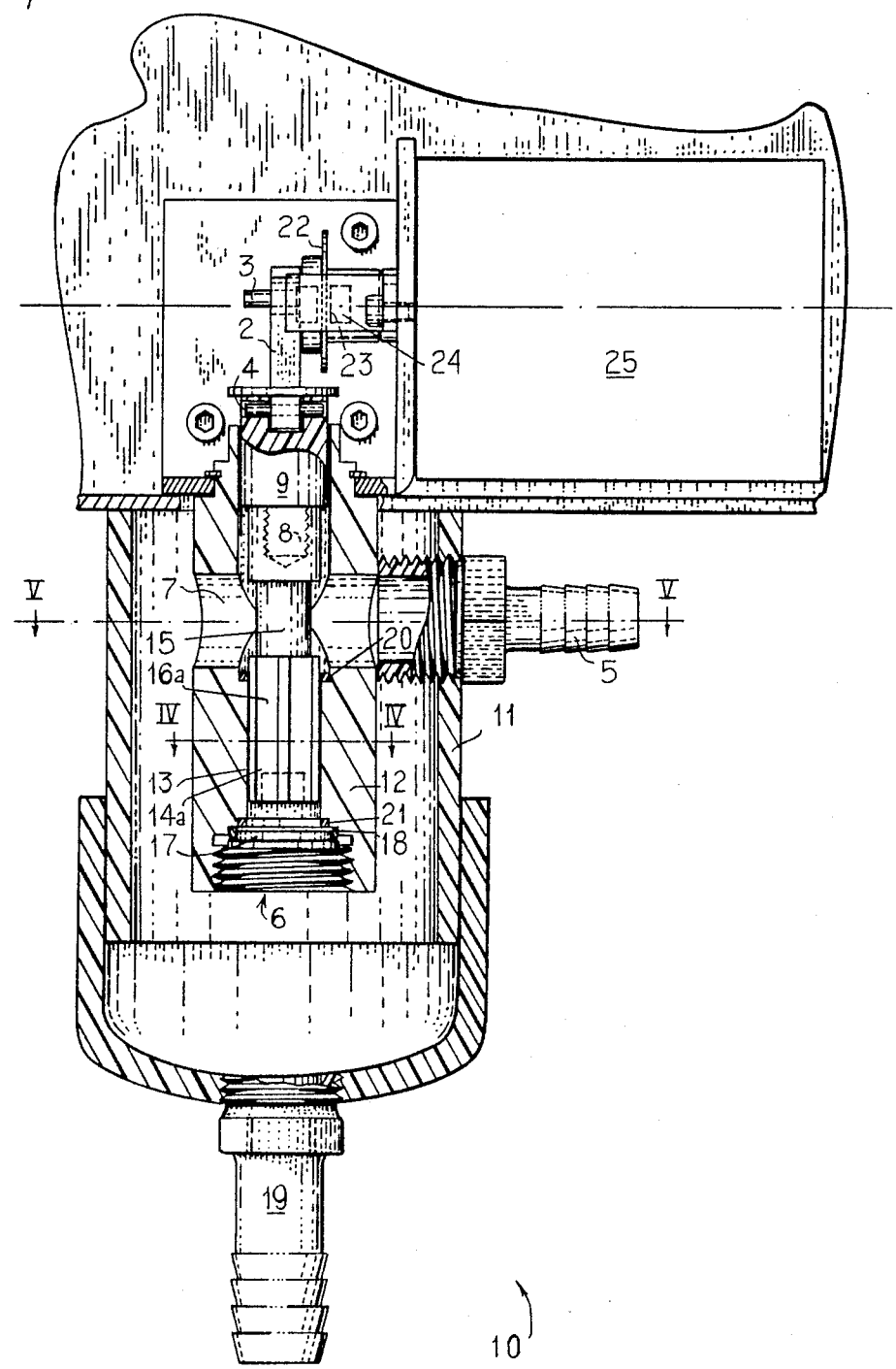
FIG. 2 is a longitudinal cross-section through the detector according to FIG. 1 in which the piston is at the top of its stroke.

As is illustrated in FIGS. 1 through 3, the apparatus, which is indicated generally by the numeral 10, comprises a vertical housing 11 that encloses a probe 6 including a flowpath member with a cylinder block 12 having a bore 13 which slidably engages a piston 14. An active segment 14a of the piston 14 fits snugly in the bore 13 and has longitudinal grooves 16 extending the length of the active segment that allow flow between it and the block 12. the bottom of the bore 13 is a cylinder head 17 that, in the preferred embodiment, threadedly engages the lower end of the block 12, allowing for ease of repair and cleaning. As shown in FIG. 2, an O-ring 18 that surrounds the upper edge of the head 17 fills a groove proximate the lower end of the bore 13 when the head is seated in the block 12, so that the O-ring forms a seal between the block and the head. The piston 14 and cylinder block 12 are preferrably made from delrin due to its low surface friction coefficient, low surface absorption and ease in machining.

Ring electrodes 20 and 21 fit into grooves formed in the bore 13 and are spaced from each other a distance approximately equal to the length of the active segment 14a of the piston 14. These electrodes are the only metallic elements in the cylinder block 11 and are preferably made of stainless steel. As the piston 14 moves, charged colloids and ions in any fluid present within the grooves 16 induce opposite and equal charges on the dielectric surfaces of the piston and of the block 12 which flow in part to the electrodes 20, 21 and which give rise to an electrical signal known as the streaming current.

As shown in FIGS. 1 and 2, an inlet nozzle 5 is provided for feeding the test flow stream into the housing 11. On entering, the stream splits with a fraction of the flow washing from the top of the active segment of the piston 14 after entering a transverse passageway 7 formed in the block 12 and the remainder of the flow plunging downwardly to the exit 19. A waist 15 formed in the piston above the grooves 16 allows a higher flow rate through the passageway 7, thereby facilitating washing the top of the segment 14a by the flow stream. When the piston 14 moves up, a small portion of the flow entering the passageway 7 is pulled into the capillary-sized channels formed between the block 12 and wall sections of the grooves 16 in the piston 14. The forces acting on the flow as it enters these channels are due not only to a vacuum created in the vicinity of the cylinder head 17 on the upstroke of the piston 14 but also to a positive pressure created at the upper ends 16a of the capillary grooves 16 by the placememt of these ends in direct contact with the flow stream in passageway 7. During the downstroke of the piston 14, fluid within the grooves 16 is expelled to fraction of the flow moving through the passageway 7. The forces acting on the fluid as it exits the grooves 16 are the result of a positive pressure on the cylinder head 17 and a negative pressure on the at the retraced upper ends 16a of the capillary grooves 16 due to the flow stream in the passageway 7 going above the active segment 14a of the piston 14.

The piston 14 is forced into repetitive upward and downward motions by a guide 9 connected to a rod 2. As is best seen in FIG. 3, one end of the rod 2 is fastened to the guide 9 by a pin 4, and the other end of the rod 2 is fastened to a crank 4. The guide 9 has a connector 8 threadedly engaging the piston 14. The crank 3 is rotated by a synchronous motor 25 at a constant rpm. In the preferred embodiment, this rotational speed is 240 RPM. An opaque half moon shaped disk 22 is affixed to the crank 3; and as it rotates, the edge of the disk 22 rotates in a slot 23 of an slotted optical switch 24. Phototransistor switching takes place when the disk 22 passes through the slot 23, momentarily blocking light between a light-emitting element and its mating phototransistor in the switch 24. A square wave pulse occurs with each revolution of the crank, and this square wave signal is then used to facilitate the detection of an alternating current generated when first one end and then the other of the active segment 14a of the piston 14 passes one of the electrodes 20, 21.

As an end of the active segment 14a of the piston 14 moves into the vicinity of one of the electrodes 20, 21, an additional charge is induced on the electrodes. Since the piston motion is reciprocal, an alternating current is generated at the frequency of the motor rotation. The alternating current generated is proportional to the net charge density on the colloids and ions in the flow stream and is called the streaming current.

In order to make this alternating signal useful, it is processed by a filtering and synchronized measurement circuit. This circuit is shown schematically on FIG. 6. The signal is first passed through a high pass filter 30 where noise below about 4.5 Hz and dc components are filtered out. It is then filtered for the signals above about 16 Hz by a low pass filter 31. A synchronous detector 32 using the input from the optical switch 24 as reference allows only the alternating current generated at the same frequency as the motor rotation, which is 4 Hz. in the preferred embodiment, to be considered. The output of the synchronous detector 32 is processed by a dc filter 33 to make a filtered dc current for the input to the indicating and control circuit 34.

Figure 6:
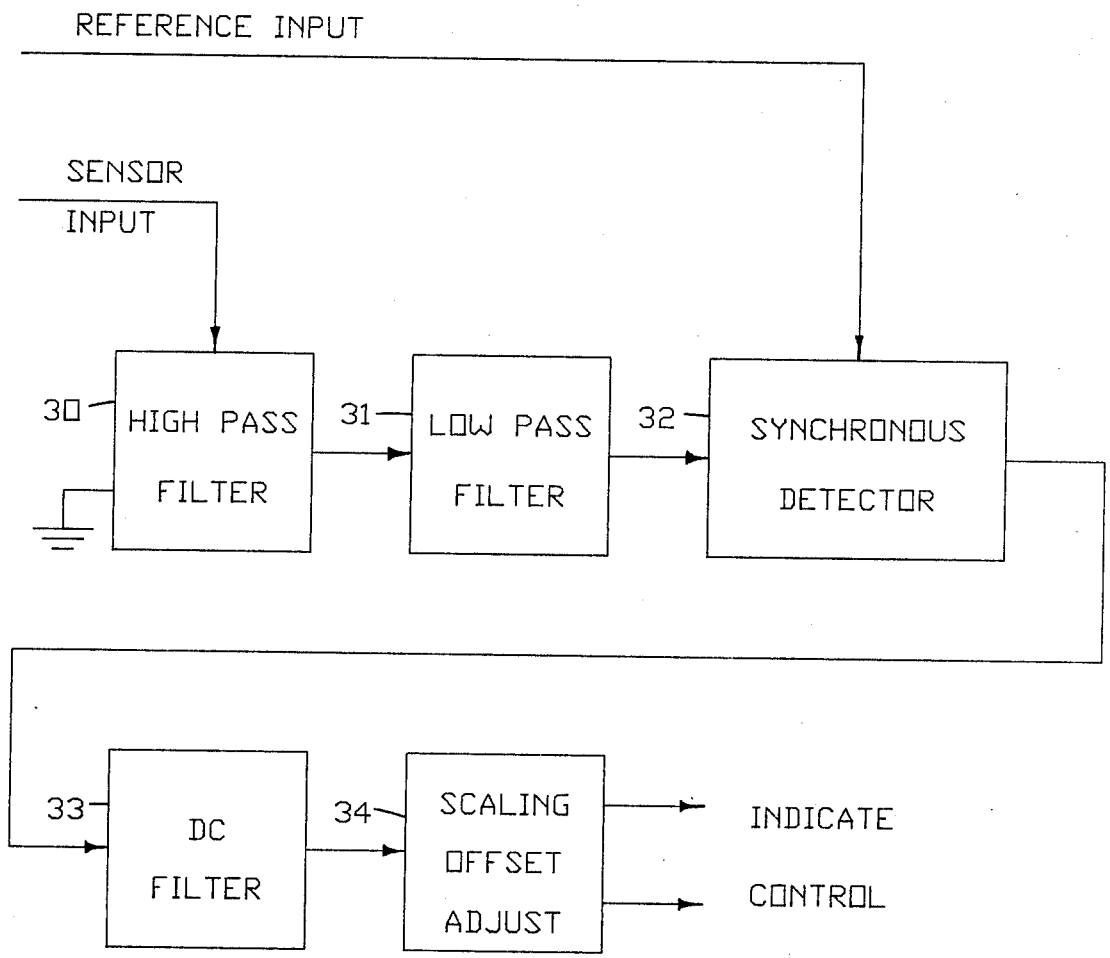
FIG. 6 shows a schematic of the signal processing equipment.

Since the electrodes 20, 21 are constantly washed during operation, the strength of the streaming current signal generated is sufficient to have a readout and control device with the circuit shown in FIG. 6 and described hereinabove which can be remotely situated from the apparatus 10 at distances up to 1000 feet from it.

Having described the invention, what is claimed is:

1. In an apparatus for determining a function of the electric charge condition in a flowable liquid media containing electrical charge influencing species, said apparatus comprising:
   a. a substantially vertical tubular flowpath member made of an electrical insulating material which has an open end on the top and a closed end on the bottom, said member having a through passageway disposed transversely to the longitudinal axis of said member, the passageway being disposed so that it may be substantially filled with said flowable liquid media;
   b. a reciprocating element whose outer wall, at least, is electrically insulating and which is disposed in slidable relationship within said flowpath member, said reciprocating element having an active segment, a substantial portion of the active segment being disposed downwardly of the transverse passageway, the segment having a transverse cross-section such that the segment fits adjacent to but has a plurality of wall sections spaced from the contiguous wall of the flowpath member forming capillary-sized flow channels when the element reciprocates in said flowpath member;
   c. a pair of spaced sensing electrodes located within said flowpath member, the first said sensing electrode being near the closed end of said flowpath member and a second said sensing electrode nearer the transverse passageway with both electrodes being so disposed as to be contacted by said flowable liquid media entering or leaving said flow channels;
   d. means for admitting said flowable liquid media to said flowpath member so that there is no stagnation within the flow of the liquid media proximate entrances to said flow channels;
   e. means for directing the discharge of the flowable liquid media from said passageway away from the flowpath member so that there is very little tendency for any separation to occur in the media in the vicinity of the flowpath member;
   f. means for moving the reciprocating element in said flowpath member so that it reciprocates at a constant frequency; and
   g. means coupled to said first and second spaced sensing electrodes for detecting, filtering and amplifying an alternating current flowing between said first and second sensing electrodes that is generated at the frequency of the reciprocating element.

2. The apparatus according to claim 1 wherein the active segment of the reciprocating element is further characterized as having grooves which extend longitudinally along the length of the active segment, the grooves and the wall of the flowpath member forming said capillary-sized channels.

3. An apparatus for measuring the streaming current in a sample flow stream of a fluid containing charged species such as ions and colloids comprising:
   a. a housing having an inlet nozzle through which the flow stream can enter;
   b. a flowpath member having a transverse passageway through which said stream can flow, the centerlines of the passageway and of the inlet nozzle being generally aligned with each other, cross-sections of the passageway which are generally parallel to the direction of the flow of the stream being dimensioned so that the total pressure of the flow stream is not substantially reduced as it moves through the passageway;
   c. the flowpath member having a capillary-sized channels which are fluidly connected to the transverse passageway, entrances to the channels being washed by the stream flowing through the passageway, thereby greatly reducing any settling of heavy particles near the entrances;
   d. a reciprocating element whose outer wall, at least, is electrically insulating and which is disposed in slidable relationship within said flowpath member, said reciprocating element having an active segment, a substantial portion of the active segment being disposed downwardly of the transverse passageway, the segment having a transverse cross-section such that the segment fits adjacent to but has a plurality of wall sections spaced from the contiguous wall of the flowpath member forming said capillary-sized flow channels when the element reciprocates in said flowpath member;
   e. two ring electrodes that are vertically separated from each other in the flowpath member and which are disposed in contact with the fluid entering or leaving said channels;
   f. means for moving the reciprocating element in said flowpath member so that it reciprocates at a constant frequency; and
   g. means coupled to said ring electrodes for detecting an alternating current flowing between said electrodes that is generated at the frequency of the reciprocating element.

4. The apparatus of claim 3 wherein the centerlines of the capillary-sized channels and of the transverse passageway are further characterized as being disposed perpendicular to each other, so that fluid discharged from the channels to the passageway enters a region in which there is a negative pressure, thereby facilitating a sucking of the sample into the flow stream and further reducing the likelihood of any settling of heavy particles in the channels.

5. The apparatus according to claim 3 which further comprises the housing having a vertical drain channel which surrounds the flowpath member, so that the flow stream leaving the transverse passageway drains rapidly downwardly and in the direction toward which heavier particles tend to settle, thereby helping to keep any floc or grit present suspended in the flow stream after its discharge from the transverse passageway.

6. The apparatus according to claim 2 which further comprises means coupled to said ring electrodes for filtering and amplifying said alternating current.

7. The apparatus according to claim 6 wherein the alternating current is further characterized being of sufficient amplitude for a signal to be sent to a remote readout and control device situated up to one thousand feet from the electrodes.

* * * * *

UNITED STATES PATENT AND TRADEMARK OFFICE
CERTIFICATE OF CORRECTION

PATENT NO. : 4,769,608

DATED : Sep. 6, 1988

INVENTOR(S) : Robert L. Bryant and Charles R. Veal, Jr.

It is certified that error appears in the above-identified patent and that said Letters Patent is hereby corrected as shown below:

On the title page, item [76], add the following inventor:

--Charles R. Veal, Jr.,
Norcross, Ga. 30071--.

Signed and Sealed this

Twentieth Day of August, 1991

Attest:

HARRY F. MANBECK, JR.

*Attesting Officer*  *Commissioner of Patents and Trademarks*